United States Patent [19]

Wadlow

[11] Patent Number: 4,801,209
[45] Date of Patent: Jan. 31, 1989

[54] PROCESS AND APPARATUS FOR ANALYZING A GASEOUS MIXTURE AND A VISIBLE EMISSION SPECTRUM GENERATOR THEREFOR

[75] Inventor: David Wadlow, Basking Ridge, N.J.

[73] Assignee: The BOC Group, Inc., Montvale, N.J.

[21] Appl. No.: 45,336

[22] Filed: May 4, 1987

Related U.S. Application Data

[63] Continuation-in-part of Ser. No. 822,457, Jan. 17, 1986, abandoned.

[51] Int. Cl.[4] .......................................... G01N 21/68
[52] U.S. Cl. .................................. 356/417; 356/311; 356/316; 364/498
[58] Field of Search ............... 356/311, 313, 315, 316, 356/417, 303; 364/497, 498

[56] References Cited

U.S. PATENT DOCUMENTS

| | | |
|---|---|---|
| 2,934,907 | 5/1960 | Scofield . |
| 2,934,908 | 5/1960 | Latimer . |
| 2,967,451 | 1/1961 | Farrall . |
| 3,025,745 | 3/1962 | Liston . |
| 3,428,401 | 2/1969 | Buzza . |
| 3,545,863 | 12/1970 | Ault et al. . |
| 3,586,441 | 6/1971 | Smith et al. . |
| 3,600,567 | 8/1971 | Varnela ............................... 364/498 |
| 3,610,759 | 10/1971 | Wood, Jr. . |
| 3,612,686 | 10/1971 | Braman et al. . |
| 3,704,952 | 12/1972 | Bird . |
| 3,951,607 | 4/1976 | Fraser . |
| 3,996,010 | 12/1976 | Fraser . |
| 4,148,612 | 4/1979 | Taylor et al. . |
| 4,150,951 | 4/1979 | Capelle et al. . |
| 4,195,641 | 4/1980 | Joines et al. . |
| 4,197,095 | 4/1980 | White, Jr. et al. . |
| 4,267,572 | 5/1981 | Witte ................................... 364/498 |
| 4,309,187 | 1/1982 | Dodge, III et al. . |
| 4,415,264 | 11/1983 | Wittmer . |
| 4,660,151 | 4/1987 | Chipman et al. .................... 364/498 |

FOREIGN PATENT DOCUMENTS

| | | |
|---|---|---|
| 1017072 | 1/1966 | United Kingdom ................. 364/498 |
| 1576141 | 10/1980 | United Kingdom . |

Primary Examiner—F. L. Evans
Attorney, Agent, or Firm—Chris P. Konkol; Larry R. Cassett

[57] ABSTRACT

There is disclosed a visible emission spectrum generating assembly for a gaseous mixture comprising a chamber for receiving the gases to be analyzed, electrodes positioned externally about the chamber and longitudinally disposed with respect to one another, an rf energy source connected to the electrodes to establish a current therebetween for generating the visible emission spectra of the gaseous mixture to be analyzed and at least one photodetector device disposed proximate the chamber to receive the thus generated light or visible emission spectra. The process and apparatus of the present invention also include a data processing device for evaluating the spectral signals received by the photodetector device and suitable display and/or recording assemblies.

20 Claims, 4 Drawing Sheets

PROCESS AND APPARATUS FOR ANALYZING A GASEOUS MIXTURE AND A VISIBLE EMISSION SPECTRUM GENERATOR THEREFOR

CROSS-REFERENCE TO RELATED APPLICATION

This application is a continuation-in-part of my copending application, Ser. No. 06/822,457, filed Jan. 17, 1986, now abandoned, and having a common assignee.

FIELD OF THE INVENTION

This invention relates to a process and apparatus for analyzing gaseous mixtures using the method of visible emission spectroscopy and more particularly to a process and apparatus for continuously measuring the amount of one or more selected gases in a multigas mixture.

BACKGROUND OF THE INVENTION

In the recovery of permanent gases (i.e., gases with very low boiling points normally found in the vapor phase), such as argon, helium, oxygen and other atmospheric gases, it is desirable to adjust processing conditions to reduce substantially amounts of a contaminant gas and thereby improve production rates of the extraction product whether in liquid or gaseous form. In the recovery of argon from atmospheric air, for example, the concentration of the nitrogen component can vary over one or more orders of magnitude from tens to thousands of parts per million in response to relatively small changes in temperature, flow rate, pressure and other environmental plant conditions. In the past the nitrogen concentration has been controlled by monitoring temperature levels on certain trays and adjusting production rates of argon withdrawn from the auxiliary rectification tower, such as disclosed in U.S. Pat. No. 2,934,908 to Latimer, or by adjusting the reflux to the primary rectification unit, similarly in response to temperature levels, such as disclosed in U.S. Pat. No. 2,934,907 to Scofield. Adjustment to process conditions suffers from delays in response to sensed conditions inherent in the operation of the rectification process. More efficacious operation of the rectification process can be achieved by actual analysis of the nitrogen content in the process stream to be treated in the secondary rectification tower for maintaining the nitrogen content within a desired range, e.g., 20 to 2000 parts per million (ppm).

Qualitative and quantitative analyses of atomic or molecular species in the vapor phase by means of their absorption or emission spectra are well known in analytical chemical techniques. In atomic absorption spectroscopy, a beam of light is passed through a vapor containing the atomic species to be analyzed and the amount of the species present is determined by the amount of light absorbed by the vapor. In visible emission spectroscopy, the atomic species in the vapor phase are excited to emit light and the spectrum and intensity of the emitted light are analyzed to determine which species are present and the concentration of each. Various methods of exciting atomic species to emit radiation have been used, such as arcs, sparks, and flames. It is also known to excite the atomic species by contact with metastable atoms of an excited, relatively inert gas in a flowing gaseous medium.

In U.S. Pat. Nos. 3,951,607 and 3,996,010 issued to Robert B. Fraser on April 20 and Dec. 7, 1976, respectively, there is disclosed a gas analyzer for pulmonary uses where the gas to be analyzed is passed through an analyzing chamber including electrodes which are in contact with the gas for generating an emission atomic or molecular spectrum representative of the gaseous mixture which is sensed by detection devices provided with filters of diverse transmission characteristics wherein the information from each device is quantified (by computer) and the response displayed as indicative of the quantity of each component of the gas. Such analysis provides data for periods of time, but suffers from unanticipated spectral responses resulting from contamination, such as by oxidation of the internal electrodes.

There is a clear need for a method and apparatus for multicomponent gas analysis which is highly sensitive and of a large linear dynamic range and is capable of analyzing more than a single component thereof using relatively simple and reliable apparatus with minimal interference effects.

SUMMARY OF THE INVENTION

The present invention is directed to apparatus and to a method for analyzing from samples the composition of an on-line multigas mixture continuously in real time by generating and analyzing emission spectra in an apparatus comprised of a chamber for receiving the gas to be analyzed, electrodes positioned externally about the chamber and longitudinally disposed with respect to one another, and an rf energy source connected to the electrodes to establish a current therebetween for generating the emission spectra of the gaseous mixture to be analyzed and at least one detector (typically a photodetector device) disposed proximate the chamber to respond to the resultant emission spectra.

The emission spectra are cyclically filtered at carefully selected wavelengths characteristic of the gases of interest in the mixture before application to the photodetection device. There follows sampling apparatus for measuring the intensities of the detected emissions at the selected wavelengths and for correlating these intensities according to an experimentally derived algorithm in order to effect a quantitative measure of the respective concentrations of the desired gas being extracted and its principal contaminant gas. The algorithm is evaluated in a dedicated microcomputer whose output is displayed conventionally. The emission spectrum typically useful with the present invention extends from approximately 200 nanometers to 900 nanometers.

In an illustrative gas mixture which has been analyzed using the apparatus and method of the present invention, the noble gas argon is being extracted from atmospheric air which has been reduced to a mixture which typically comprises ten to fifteen percent of argon and the balance oxygen with only traces of nitrogen. The nitrogen concentration may vary within the range of 20 to 2000 ppm using previously established control procedures. However, it is desirable to control it closer to an optimum level within that range. The value of the optimum level depends on individual process conditions. The emission spectrum typically useful for this particular mixture of gases is approximately 250 nanometers to 750 nanometers.

BRIEF DESCRIPTION OF THE DRAWING

A better understanding of the present invention will become more apparent upon consideration of the detailed description thereof, especially when taken with the accompanying drawings, wherein like numerals designate like parts throughout, and wherein.

DETAILED DESCRIPTION OF THE INVENTION

Figure 1:
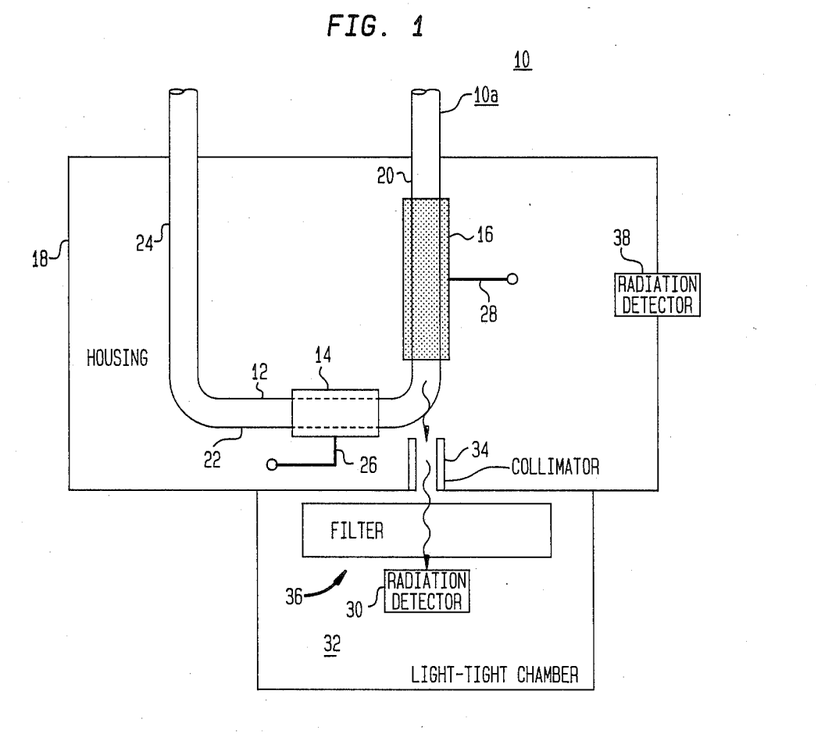
FIG. 1 is a plan view of an apparatus in accordance with the present invention for generating and sensing emission spectra.
Figure 2:
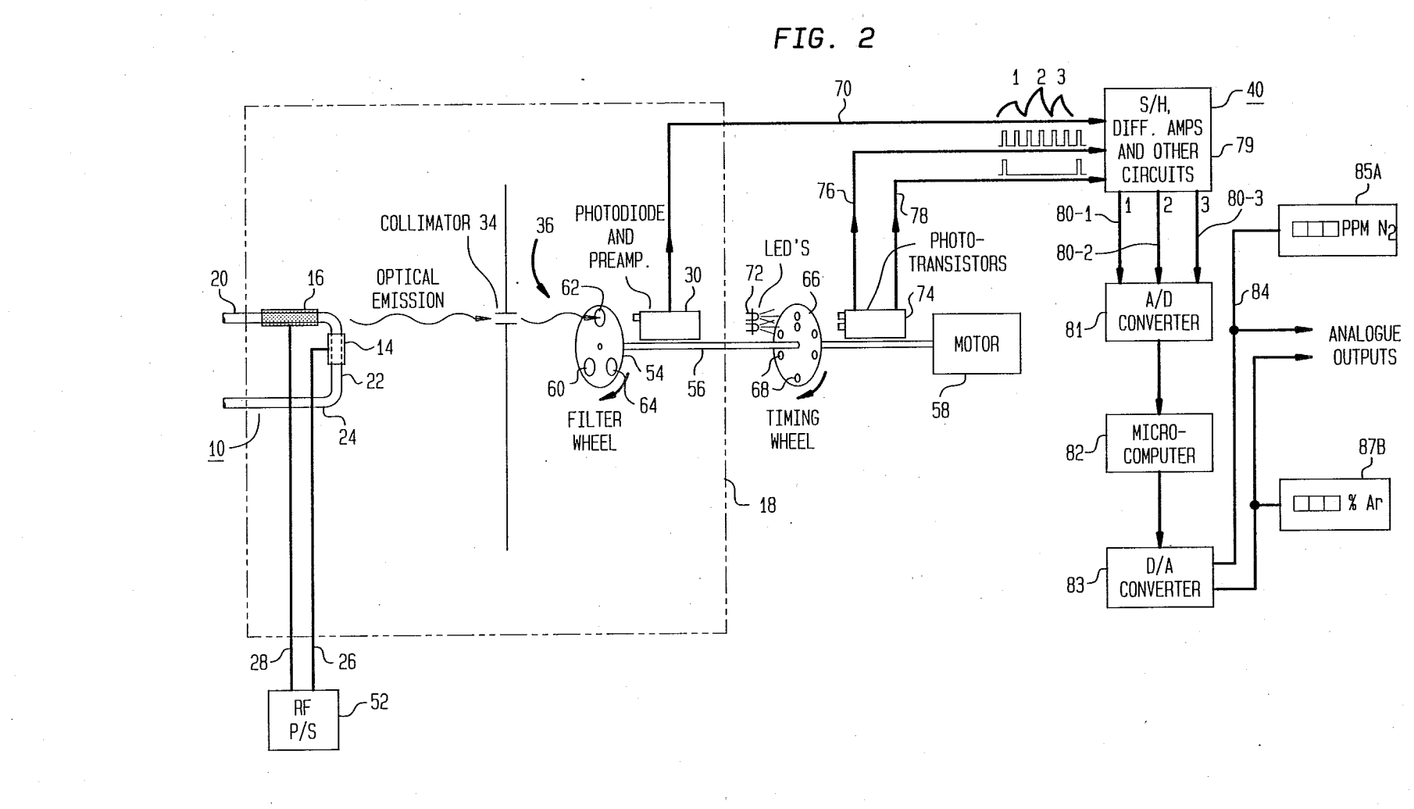
FIG. 2 is a schematic diagram of apparatus in accordance with the present invention for analyzing a gaseous mixture including the apparatus of FIG. 1 in real time.
Figure 3:
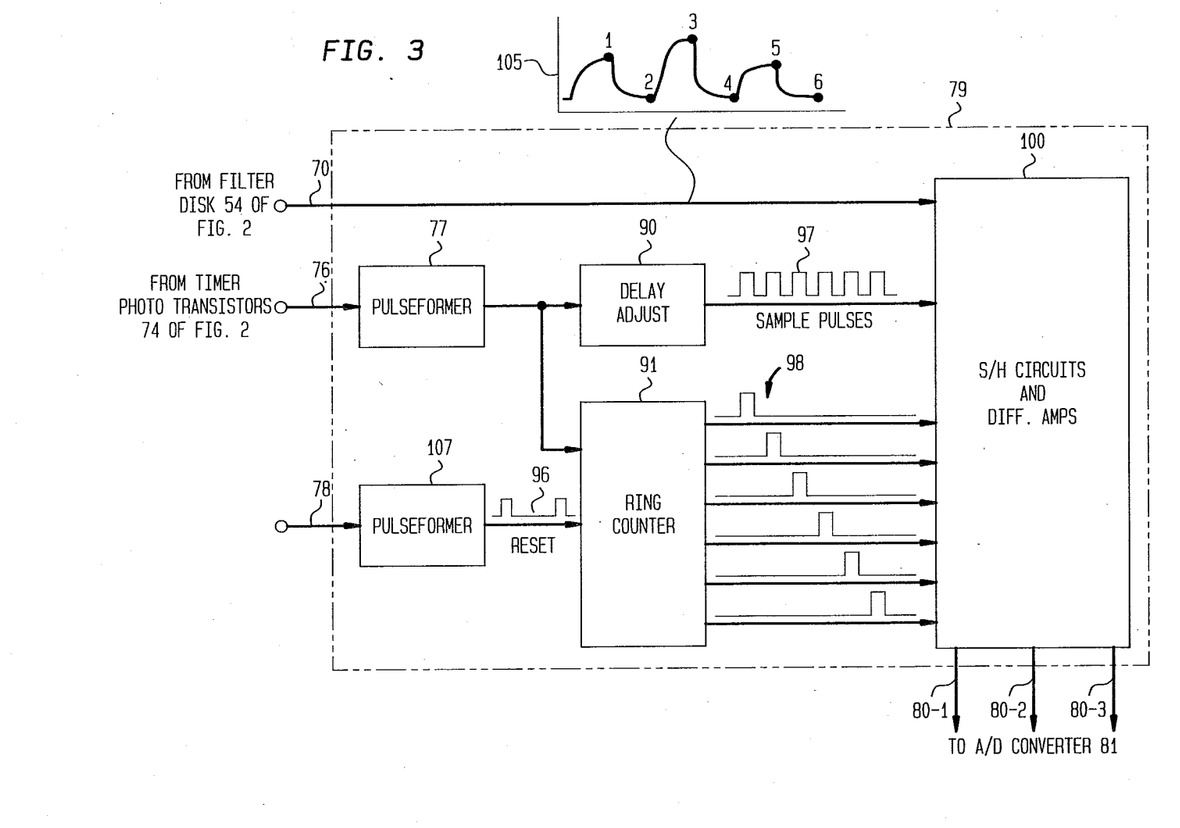
FIG. 3 is a more detailed block diagram of some of the apparatus of FIG. 2.

Referring now to FIG. 1, there is shown emission apparatus 10 in accordance with the present invention which comprises a housing 18, and emission cell 10a comprising a U-shaped conduit 12 having separated cylindrical electrodes 14 and 16, a first radiation detector 30 (typically a photodiode), an essentially light tight chamber 32, a collimator 34, a filter assembly 36 and a second radiation detector 38 (typically a photodiode) which is optional. A sample of gas being analyzed is flowed through conduit 12 at a controlled pressure and flow rate. The present invention uses the apparatus shown in FIG.'s 1, 2 and 3 and a method which utilizes emission spectrosocopy for measuring the composition or relative concentration of at least one component gas of a multi-component gas mixture. The spectrum used is typically the visible spectrum which is defined herein as 200 to 900 nanometers (nm).

Conduit 12 comprises a base portion 22 and leg portions 20 and 24 which extend through housing 18. Cylindrical electrodes 14 and 16, formed preferably of non-corrosive conducting materials, surround sections of leg portions 22 and 20, respectively, of conduit 12 in a spaced-apart mutually longitudinal relationship. Typically electrode 14 is solid and electrode 16 is meshed. Conduit 12 is transparent, preferably of glass or quartz, to permit transmission of the visible spectra to an optical detection device 30 (also shown in FIG. 2). Electrodes 14 and 16 are mounted externally of conduit 12 to avoid exposure to the gases being measured and are connected by respective conductors 26 and 28 to a conventional RF (radio-frequency) power source 52 which is not shown in FIG. 1 but is shown in FIG. 2. Electrode 16 is typically grounded. It has been found that the ratio of the areas of the hot and ground electrodes is one factor which determines the voltage distribution within the sheath of the plasma created by the application of RF energy to the emission cell.

Gas flowing through conduit 12 experiences an R.F. glow discharge reaction in the region of conduit 12 between electrodes 14 and 16 when power source 52 is on. Light emitted as a product of the glow discharge reaction is collimated through collimator 34 and illuminates photodiode 30. Optional detector (photodiode) 38 is positioned within housing 18 to sense the radiation therein and thereby to provide an operational on-means of the generation of electromagnetic radiation within housing 18 during analysis of a gaseous mixture.

The voltages present at cell electrodes 14 and 16 give rise to an electric field which tends to accelerate ions and electrons in the enclosed gas and to form a plasma which is manifested by a stable glow discharge. In the plasma electrons, ions and neutral atoms and molecules are in continuing collision with each other. Visible photons are thus emitted. There are many discrete energy levels at which photons can be emitted and the wavelengths of these photons is known to be inversely proportional to the energy of the transitions between levels. If only one gas species is present a continuous spectrum of visible radiation is observed and the gas can be identified from its characteristic pattern of wavelengths and lines of intensity. Spectra of individual gases have been catalogued.

For background information on the general subject of the interpretation of spectral signals in gas compositions, reference is made to the book by Bochkov et al. published in 1965 by Academie Press and entitled "Spectroscopic Analysis of Gas Mixtures".

The emission spectrum emanating from a discharge within a mixture of gases is the sum of all the photons being emitted with the result that the combined spectrum is not a linear sum of the individual spectra. The relative intensities of the spectral lines associated with the individual gases are not preserved due to what is known as the matrix effect. Deconvolution or separation of the individual spectra from a combined spectrum is thus more of an art than a science. Complexity increases rapidly in multigas mixtures.

In general matrix effects are obtained whenever two or more gases are mixed. Furthermore, the effects are invariably nonlinear, which is to say that the change in shape of the emission spectrum of a particular gas is dependent not only on the quantity of another gas with which it is mixed, but also on the characteristics of the other gas or gases added. With a relatively simple binary mixture of, say, oxygen and argon, it is possible in many cases to determine empirically the variation in peak height of a particular feature versus composition. Provided that this variation is monotonic, it is feasible to use this relationship to act as an indication of the relative amounts of the two gases present. However, when more than two gases are present in a mixture, the relationships between any set of the various relative heights of emission peaks and overall gas composition become too complex for reliable interpretation by prior methods.

Despite the inordinate complexity of multigas analysis I have found that for at least several multigas mixtures there exists an algebraic relationship, or more properly a family of such relationships, which does accurately and uniquely describe the composition of a multigas mixture over a specific range of compositions in terms of specific components of the spectral emission from that gas mixture. Such an analytical algorithm can then be embedded in the program memory of a dedicated microcomputer capable of running that algorithm and continually recalculating the gas composition based on spectral data supplied by the optical detector. There then exists a dedicated, real-time gas analyzer.

Given a stable source configuration, the first step is to retrieve the visible emission spectrum for each of the pure gases of interest for different source regions and operating conditions. The mixture of interest for analysis in the preferred embodiment consists of percentage-level argon and oxygen with parts per million (ppm) levels of nitrogen to be monitored and controlled. It is to be noted that the intensity of the nitrogen signal depends not only the nitrogen concentration but also on the argon/oxygen ratio. The very low level of nitrogen means that it is desirable that the rf excitation source favor the generation of nitrogen emission energy compared with the more abundant argon and oxygen in the gas. This is accomplished by positioning the optical detector longitudinally with respect to the leg about which is wrapped the ground electrode. The spectrum varies along the length of the cell. It is preferred to select a region of the cell near electrode 16. There is a tendency for the nitrogen peaks to be stronger in this area. I have found this positioning attitude makes it possible to develop an emission source that provides sufficient light output at an intensity and stability commensurate with a good signal-to-noise ratio and a rapid retrieval rate.

Figure 4:
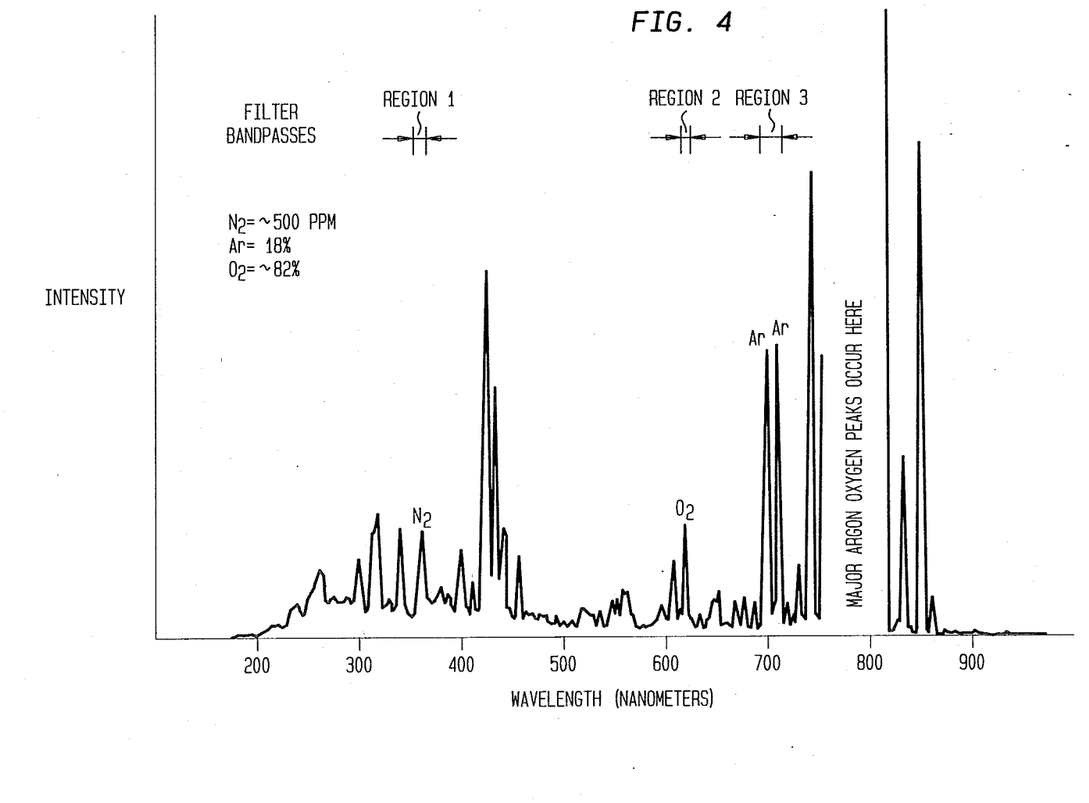
FIG. 4 is a representative spectrogram of a mixture of argon and oxygen with traces of nitrogen useful in explaining this invention.

The second step is to find a broad set of candidate wavelength regions by which interferences among spectral lines are not overpowering and where intensities are of comparable magnitude. FIG. 4 depicts the emission spectrum corresponding to a gas mixture consisting of 500 ppm nitrogen, 18% argon and the balance oxygen. The abscissa represent wavelengths in nanometers and the ordinates represent light intensity in arbitrary units. The gap in the vicinity of 800 nm represents off-scale argon and oxygen lines. A number of different peaks are identified as resulting from each of the component gases. A series of spectra were retrieved over a rang of cell operating pressures. It was found that intensity declined with cell pressures in the range of 2.75 to 5.75 torr (one Torricelli =1/760 atmosphere). However, it was noted that the rate of intensity decline of the different regions was most similar at pressures greater than about 4 torr. At higher pressures the response time of the cell declines (at a constant gas sampling rate) along with signal intensity. Accordingly, a compromise pressure of 4.0 torr is assumed.

The third step is to learn if and how the various light intensities are related to gas composition. To accomplish this task a large number (50 to 100 different compositions were used to provide a workable data set) of emission spectra were generated from known gas proportions using a monochromator and the resultant spectra were digitized. The spectra were next split up into wavelength regions and for each region intensities of light emission were integrated and their relationships to nitrogen and argon concentrations were identified. From this analysis it became possible to determine the minimum number o±regions needed to correlate reliably with these concentrations. Application of well known principles of linear regression reveals that a high correlation exists with continuous, well behaved functions of the integrated light intensities within three of the selected regions. As shown in FIG. 4, these three regions are centered on these emission peaks:

1. 358 nm peak due to nitrogen;
2. 617 nm peak due to oxygen; and
3. 697 and 707 nm twin peaks due to argon.

The final step is to derive an analytical function or algorithm. The integrated light intensities from each of the three regions can be denominated as V1, V2 and V3. Two of these values can be normalized with respect to the third in order to facilitate two-dimensional plotting. Thus, two independent variables are made available as:
$R1 = V3/V1$; and
$R2 = V2/V1$.

The relationship between each gas component and the independent variables R1 and R2 can in fact be described by a set of full quadratic equations with appropriate boundaries. The analytic response functions thus derived are of the following forms:

$$\text{Nitrogen} = a0 + a1Z1 + a2Z2 + a3Z1^2 + a4Z1Z2 + a5Z2^2$$

$$\text{Argon} = b0 + b1Z1 + b2Z2 + b3Z1^2 + b4Z1Z2 + b5Z2^2.$$

where the a's and b's are numerical coefficients and $Z1 = R1 - M1$, $Z2 = R2 - M2$, and M1 and M2 are mid-values of the respective data groups.

If these equation do not yield solutions of the desired accuracy because of possible discontinuities, the responses can be segregated into adjoining segments.

In the preferred embodiment the equations were derived for three segments: $A = R2 < = 1.62$; $B = 1.62 < R2 < = 1.88$; and $C = R2 > 1.88$. The resultant midpoint values and coefficients adopted are shown in the following Table I:

| Coefficient | A | B | C |
| --- | --- | --- | --- |
| a0 | 313.60 | 196.57 | 87.41 |
| a1 | −211.64 | −259.27 | −227.14 |
| a2 | −626.94 | −424.81 | −211.21 |
| a3 | −116.41 | −79.41 | −67.03 |
| a4 | −126.24 | 8.306 | 104.31 |
| a5 | 892.24 | 387.65 | 107.89 |
| b0 | 13.88 | 12.53 | 8.47 |
| b1 | 25.90 | 21.34 | 14.40 |
| b2 | −19.00 | −14.89 | −6.172 |
| b3 | 9.792 | 7.604 | 4.316 |
| b4 | −32.89 | −22.03 | −14.49 |
| b5 | 17.20 | 16.87 | 1.860 |
| M1 | 0.8185 | 0.884 | 0.850 |
| M2 | 1.537 | 1.738 | 2.1415 |

Referring again to FIG. 2, filter assembly 36 is comprised of rotating filter wheel 54 connected by shaft 56 to motor 58 and is provided with three filter elements 60, 62 and 64. The filter elements 60, 62 and 64 have spectral transmission characteristics which are matched to certain features of the visible emission spectra emanating from the excited mixture of nitrogen, argon and oxygen. The bandwidths of the filter elements are matched to the molecular species in the gaseous mixture in breadth sufficient to allow transmission of sufficient light at the wavelengths of interest without undue contribution from neighboring features of the spectrum which are not needed. The bandwidth of each filter element is defined as the width of the bandpass at some arbitrarily defined proportion of the peak transmission. Generally, as previously discussed, the particular site from which the visible emission is sensed is preferably located at a point where the intensity of the band for each species is about the same thereby to minimize gain effects on the photodiode which may result when the photodiode is subjected to extreme ranges between high and low intensities of light emission.

A timing wheel 66 is mounted on shaft 56 and is provided with a plurality of equally spaced-apart apertures 68 with one-half of such apertures aligned with respect to the filters 60, 62 and 64, it being understood that an electronic circuit may be employed to adjust and compensate for mechanical misalignment. Radiation detector 30 is coupled to a conductor 70 for transmitting information to a data processing section 40. Timing wheel 66 is provided with two light emitting diodes 72 and phototransistors 74 to receive information via apertures 68 and transmit timing information via conductors 76 and 78 to data processing section 40.

In data processing section 40, the information from radiation detector 30 comprised of a repeating series of the three spectral intensity signals is passed via conductor 70 and is correlated with the signals received from the phototransistors 74 transmitted via conductors 76 and 78 and wherein the data processing section 40 is provided with hardware to continually translate the spectral signals into signals proportional to the peak intensity of each waveform.

Data-processing section 40 comprises sample-and-hold circuits (S/H), differential amplifiers, and other circuits, all denoted by number 79, an analog-to-digital converter 81, digital microcomputer 82 and digital-to-analog converter 83. Circuits 79 receive the train of exponential waves from photodiode 30 over lead 70 resulting from the integration of energy in the exemplary three filters on filter wheel 36. Circuits 79 are also supplied with two timing signals derived from timing wheel 68. Both timing signals are cyclic with the rotation of shaft 56. The first timing signal provides two sampling instants through a conventional ring counter for each selected bandpass. The second timing signal establishes the sequence in which each of the spectral signals generated is read.

FIG. 3 shows details of circuits 79 of FIG. 2. The top input line 70 shows a voltage waveform 105 which varies with time that represents spectral signals from collimator 34 and filter wheel 54 that are converted into electrical waves in photodiode and amplifier 30 in a conventional manner and appear on output line 70 as separate and sequential wave samples from each of the individual filters in wheel 54. The sampling and cycle timing signals generated by the apertures in timing wheel 66 are converted into electrical signals in phototransistor block 74 in a conventional manner and appear on lines 76 and 78. These signals are referred to a fixed base level in pulseformers 77 and 107, which can constitute conventional operational amplifiers. The sample timing pulses from pulseformer 77 are subjected to a delay adjustment in block 90 and are applied to sample and hold block 100 in the form of timing pulses shown in waveform 97. The sample timing pulses are also applied as clock pulses to ring counter 91. Similarly, reset pulses of the form shown in waveform 96 and occurring at the cyclic rate of timing wheel 66 are formed in pulseformer 107 from signals appearing on lead 78 from phototransistor 74. Ring counter 91, which is typically composed of conventional JK-type flip flops, is driven by clock pulses from pulseformer 77 and reset pulses from pulseformer 107. Ring counter 91 delivers a group of six gating pulses (waveforms 98) to sample and hold block and differential amplifier block 100 so that the delay-adjusted sampling pulses from delay adjust block 77 can respond to the respective peak (designated 1, 3 and 5 on waveform 105) and baseline (designated 2, 4 and 6 on waveform 105) pulses of the spectral signals shown in waveform 105. The respective peak and rest levels held in sample and hold portion of block 100 are then made available to differential amplifiers portion of block 100 which then generate analog voltage signals proportional to the energy levels in the selected bandwidths of the complete spectral signals. These signals are delivered on leads 80-1 80-2 and 80-3 to converter 81 and microcomputer 82 for analysis according to the algorithms set forth above.

Referring again to FIG. 2, converter 81 digitizes these analog magnitudes into suitable input signals for microcomputer 82. Microcomputer 82 processes these applied signals in accordance with the algorithm set forth above using the coefficients in Table 1 to generate signals proportional to the amount of the contaminant nitrogen in the mixed gas being analyzed and the percentage of the desired argon noble gas. Digital output signals from computer 82 are coupled to inputs of D/A Converter 83 which converts them into analog form. The resultant analog signals appear on leads 84 and 86 to drive suitable display devices 85A and 85B, respectively. Device 85A displays by direct readout the parts-per-million nitrogen content and device 85B, the percentage of argon in the mixture.

In operation, the gaseous mixture to be analyzed is introduced into conduit 12 of emission cell 10 via leg 20 at a pressure of from about 1 to 10 torr. Electrodes 14 and 16 are in spaced longitudinal relationship about the conduit 12 of from $\frac{1}{8}$ to 10 inches and a source of RF energy connected thereto to generate the light emission spectra as generally determined by the electrical properties of the cell wall material. Conduit 12 is formed of a dielectric material, such as quartz or like transparent material, for example, glass, i.e., which also acts as an electrical insulator. The generated spectral emission must be capable of visual observation or sensing by a radiation detector with minimal attenuation. The conduit 12 may be formed into any desired geometry depending on the gaseous mixture to be analyzed, the visible emission spectra to be generated and its spectroscopy given the desire to evaluate wavelength peaks of like amplitude representative of the components of the gaseous mixture.

Electrodes 14 and 16 may be formed of a suitable electrically conductive material in either solid or meshed form thereby permitting viewing or sensing at any predetermined location along the conduit 12 as best determined by a general assay of the gaseous mixture being analyzed and specifics as to inherent variables when considering process requirements of the adjunct processing equipment, e.g., trace amounts of nitrogen in an argon-oxygen gaseous mixture (4–20% argon-balance $O_2$). In the instant application as previously disclosed, it was found particularly desirable to use the visible emission spectra along the axis of the leg portion 20 of the conduit 12 with the electronic circuitry hard-wired for the composition of such aforementioned gases with appropriate filter elements 60, 62 and 64 for argon-ni-trogen-oxygen positioned in the filter orifices of the filter assembly 36.

In one illustrative example, a gaseous stream (approximately 20 SCCM) is continuously withdrawn from a gaseous conduit of an argon purification process to determine in real time the nitrogen content thereof. The nitrogen content is to range with trace concentrations of from 100 to 1500 ppm in an argon-oxygen gas mixture (4–20% argon-balance $O_2$). Outside this range the overall process will tend to break down. The gaseous stream at a pressure of 4.0 torr is introduced via leg portion 20 into conduit 12 (0.152"ID) including cylindrically-shaped solid stainless steel electrode 14 and a cylindrically-shaped mesh electrode 16 formed of stainless steel and spaced apart about 5 mm. An RF energy source of 13.56 MHz is applied to generate a visible emission spectra. The light emission from conduit 12 is viewed by radiation detector 30 via collimator 34 and filter assembly 36 along the axis of leg portion 20 of conduit 12, it being understood that the exact positioning thereof is determined by trial and error with reference to generated signals including amplitudes of each signal. Filter wheel 52 is provided with commercially available circular optional bandpass interference filters having the following details:

| Filter | Center Wavelength (nm) | Bandwidth (nm) | Comment |
|---|---|---|---|
| 1 | 360 | 11 | Corion P10-360-F |
| 2 | 620 | 10 | Corion S10-620-F inclined 12° to incident angle |
| 3 | 700 | 25 | Corion S25-700-F + neutral density filter |

The signals received on radiation detector 30 are converted into three analog voltages corresponding to each optical channel from which gas composition is computed in real time from the magnitude. In the aforementioned example, use was made of a filter wheel to disperse the emission spectra; however, it is to be understood by one skilled in the art that a spectrograph or rapid scanning monochromator could be used in conjunction with one or more optoelectronic detectors or a plurality of photodetectors with individual fixed filters.

Simplified for ease of understanding, the basic principles of this invention can be summarized as follows:

The invention is a technique for measuring the composition, or relative concentration, of at least one component of a multicomponent (two or more) gas mixture within a more or less specific range of compositions. In some applications the interest is in determining when a particular component falls outside, either above or below a specified range, as in the important application of assuring that the nitrogen component in the example nitrogen, argon and oxygen mixture remains within a desired range.

For the three-gas mixture example, the technique involves the application of radio-frequency energy to a gas mixture in order to excite visible emission which is dispersed into certain discrete spectral regions such that the gaseous composition is a function of the light intensity emanating within those spectral regions. The light intensities in the target regions are separately converted into electrical currents. By observing a sufficient number of controlled mixtures whose compositions vary over the working range of concentrations, one can devise an algorithm providing a continuum of compositional values of the component gases in terms of the light intensities observed in the chosen regions. The algorithm itself can be stored, typically in the electronic memory of a computer along with appropriate coefficients.

Subsequently, an unknown gas mixture with components within the assumed working range can be analyzed quantitatively through the application of the previously derived stored algorithm.

While the invention has been described in connection with a specific exemplary embodiment, it will be understood that many modifications will be apparent to those skilled in the art, and that this disclosure and the appended claims are intended to cover any adaptations or variations thereof. Moreover, while the invention has been disclosed in the context of a specific three-gas mixture which can be charted in two dimensions, its principles are clearly extensible into more complex mixtures where the matrix effect may be more intractable and the charting multidimensional

What is claimed is:

1. A method of analyzing a gaseous mixture of three or more atomic or molecular components from a combined emission spectrum into component magnitudes comprising the steps of:
   a. selecting from said combined emission spectrum bandpass regions at least equal in number to that of the number of component gases such that each region contains emission peaks at characteristic wavelengths identifying each individual component gas;
   b. measuring the intensity of the emission in each selected spectral region:
   c. converting the regional intensities into digital electrical signals;
   d. correlating respective ratios of adjacent converted electrical signals into indicia representative of the amounts of the individual component gases present in the mixture according to an algorithm derived from repeated observations of spectral responses extending over a range of known representative gas mixtures; and
   e. determining the relative amount of at least one of the individual component gases.

2. A method of analyzing a gaseous mixture of three atomic or molecular components X, Y and Z from a combined emission spectrum into component magnitudes comprising the steps of:
   a. selecting from said combined emission spectrum bandpass regions A, B and C at least equal to the number of component gases X, Y and Z such that each region contains emission peaks at characteristic wavelengths identifying each individual component gas;
   b. measuring the intensity of the emission in each selected spectral region A, B and C;
   c. converting the regional intensities into digital electrical signals;
   d. correlating respective ratios of adjacent converted electrical signals into indicia representative of a measure of the individual component gases present in the mixture according to the following equations:

$$G1 = a0 + a1Z1 + a2Z2 + a3Z1^2 + a4Z1Z2 + a5Z2^2,$$

$$G2 = b0 + b1Z1 + b2Z2 + b3Z1^2 + b4Z1Z2 + b5Z2^2;$$

where a0 through a5 and b0 through b5 are constant coefficients;
   $V1$ = intensity of a selected X gas spectral line in region A;
   $V2$ = intensity of selected Y gas spectral line in region B;
   $V3$ = intensity of selected Z gas spectral line in region C;
   $Z1 = R1 - M1$; $Z2 = R2 - M2$;
   $R1 = V3/V1$; $R2 = V2/V1$;
   M1 and M2 are midvalues of the numerical ranges of the values of R1 and R2, respectively; and
   e. determining the relative amount of at least one of the individual component gases.

3. Apparatus for analyzing a gaseous mixture of three atomic or molecular components X, Y and Z from a combined emission spectrum comprising:

a. means for separating said combined emission spectrum into bandpass regions A, B and C at least equal in number to that of the number of component gases X, Y and Z such that each region contains energy peaks at characteristic wavelengths identifying each individual component gas;
b. means for measuring the intensity of the emission in each separated spectral region A, B and C;
c. analog-to-digital conversion means for transforming the regional intensities into digital electrical signals;
d. calculating means for correlating respective ratios of adjacent converted electrical signals into digital indicia representative of a measure of the individual component gases present in the mixture according to the following equations:

$$G1 = a0 + a1Z1 + a2Z2 + a3Z1^2 + a4Z1Z2 + a5Z2^2,$$

$$G2 = b0 + b1Z1 + b2Z2 + b3Z1^2 + b4Z1Z2 + b5Z2^2;$$

where a0 through a5 and b0 through b5 are constant coefficients;
V1 = intensity of a selected X gas spectral feature in region A;
V2 = intensity of selected Y gas spectral feature in region B;
V3 = intensity of selected Z gas spectral feature in region C;
Z1 = R1 − M1; Z2 = R2 − M2;
R1 = V3/V1; R2 = V2/V1;
M1 and M2 are mid values of numerical ranges of the values of R1 and R2, respectively;
e. means within said calculating means for storing said equations and said coefficients;
f. digital-to-analog conversion means for transforming the solutions G1 and G2 from said calculating means into analog output signals; and
g. means responsive to the output signals from said digital-to-analog conversion means for determining the relative amount of at least one of the individual component gases as a utilizable electrical quantity.

4. The apparatus of claim 3 wherein:
component X equals nitrogen gas in a measure of parts per million;
component Y equals oxygen gas by percentage measure;
component Z equals argon gas by percentage measure; and
the means for measuring is photoelectronic means.

5. The apparatus of claim 4 wherein:
region A occupies a bandwidth of approximately 10 nm (nanometers) at a wavelength of about 360 nm,
region B occupies a bandwidth of approximately 10 nm at a wavelength of about 620 nm, and
region C occupies a bandwidth of approximately 25 nm at a wavelength of about 700 nm.

6. A method of analyzing a gaseous mixture including at least three component gases comprising the steps of:
a. applying rf (radio-frequency) energy to the mixture for generating the emission spectrum of the mixture,
b. measuring emission from said emission spectrum in at least three discrete wavelength bands in each of which the detectable emission is predominantly that of a different component of the mixture and measuring the detected emission separately in each of the bands of representative gas mixtures of known composition of the kind to be analyzed,
c. deriving from such measurements of known mixtures an algorithm usable as the program memory of an electronic computing means and storing such algorithm in the electronic computing means,
d. applying said rf energy to the gaseous mixture to be analyzed in the same manner as to the gaseous mixtures of known composition at each of the discrete wavelength bands, and
e. supplying measures of the amount of emission detected from the unknown mixture from each discrete wavelength band to the electronic computing means for generating an output which is a measure of a desired individual component of the mixture for external utilization.

7. The process of claim 6 in which the gaseous mixtures to be analyzed include three component gases and three selected corresponding wavelength bands for the detection of the amounts of energy therein.

8. The process of claim 6 in which the three component gases are argon, oxygen and nitrogen.

9. A process for generating visible emission spectra of a gaseous mixture of subsequent quantification of components thereof comprising the steps of:
introducing said gaseous mixture into a chamber including electrodes externally positioned about said chamber in spaced longitudinal relationship therebetween;
connecting said electrodes to an rf-energy source to generate said visible emission spectra;
collimating said generated visible emission spectra at a position to provide a response of substantially like intensity for each of said components of said gaseous mixture;
directing said collimated visible emission spectra to a filter assembly including filter elements wherein each filter element transmits over a wavelength region corresponding to selected spectral emission features suitable for detecting each of said components of said gaseous mixture; and
sensing filtered pulses of said thus generated visible emission spectra.

10. A process for analyzing a gaseous mixture to quantify components thereof comprising the steps of:
introducing said gaseous mixture into a chamber including electrodes externally positioned about said chamber in spaced longitudinal relationship therebetween;
connecting said electrodes to a source of rf-energy to generate visible emission spectra;
collimating said generated visible emission spectra at a position to provide a response of substantially like intensity for each of said components of said gaseous mixture;
directing said collimated visible emission spectra to a filter assembly including filter elements wherein each filter element transmits over a wavelength region corresponding to selected emission features suitable for detecting each of said components of said gaseous mixture;
sensing components of the visible emission spectra and converting the same to electric pulses representative of each of said components; and
evaluating said electric pulses to quantify said components of said gaseous mixture.

11. A method of analyzing a gaseous mixture of three or more atomic or molecular components, including at least three components X, Y, and z, from a combined emission spectrum into component magnitudes comprising the steps of:
  a. selecting from said combined emission spectrum bandpass regions at least equal in number to that of the number of component gases, including at least regions a, B, and C, such that each region contains emission peaks at characteristic wavelengths identifying each individual component gas;
  b. measuring the intensity of the emission in each selected spectral region;
  c. converting the regional intensities into digital electrical signals;
  d. correlating respective ratios of adjacent converted electrical signals into indicia representative of the amounts of the individual component gases present in the mixture according to an algorithm derived from repeated observations of spectral responses extending over a range of known representative gas mixtures; and
  e. determining the relative amount of at least one of the individual component gases with respect to the total content of the mixture.

12. The method of claim 11 or 2 in which:
component X equals nitrogen gas in a measure of parts per million,
component Y equals oxygen gas by percentage measure, and
component Z equals argon gas by percentage measure.

13. The method of claim 11 or 2 in which:
region A occupies a bandwidth of approximately 10 nm (nanometers) at a wavelength of about 360 nm,
region B occupies a bandwidth of approximately 10 nm at a wavelength of about 620 nm, and
region C occupies a bandwidth of approximately 25 nm at a wavelength of about 700 nm.

14. Apparatus for analyzing a multigas mixture from a combined emission spectrum comprising:
  a conduit for a continuous gaseous stream having a substantially right-angle bend therein;
  a first cylindrical electrode wrapped around one leg leading toward the right-angle bend in said conduit;
  a second cylindrical electrode wrapped around another leg leading away from the right-angle bend in said conduit;
  means for applying rf-energy to said first and second electrodes in series relationship to generate a visible emission spectrum from the excited gaseous mixture in said conduit;
  radiation detection means located along the longitudinal axis of the one leg and externally of said conduit for converting the light energy in the visible emission spectrum into electric signals;
  collimating means for said visible emission spectrum located along the longitudinal axis of the one leg and externally of said conduit between said conduit and said radiation detector;
  filter means for separating said visible emission spectrum into regions specific to predetermined spectral lines characteristic of component gases therein located along the longitudinal axis of the one leg and externally of said conduit between said conduit and said collimating means; and
  means for processing the electric signals from said radiation detection means into quantitative measures of the component gases in said multigas mixture.

15. A method for analyzing a multigas mixture from a combined emission spectrum comprising the steps of:
  a. streaming a gaseous mixture through a conduit having a substantially right-angle bend therein and a first cylindrical mesh electrode around one conduit leg leading toward such bend and a second cylindrical solid electrode around another conduit leg loading away from such bend;
  b. applying rf-energy to such first and second electrodes in series relationship to generate a visible emission spectrum;
  c. collimating light energy emanating form the one leg of such conduit along its longitudinal axis;
  d. filtering collimated light energy to separate the visible emission spectrum into regions specific to predetermined spectral lines characteristic of component gases therein;
  e. detecting light energy in the separated regions of the visible emission spectrum and converting the same into electric signals; and
  f. processing such electric signals into quantitative measures of the component gases in said multigas mixture.

16. Apparatus for analyzing a multigas mixture that essentially comprises four to twenty percent argon and the balance oxygen with traces of nitrogen from a combined emission spectrum comprising:
  a conduit for a gaseous stream of the mixture having a substantially right-angle bend therein;
  a first cylindrical ground electrode wrapped around one leg leading toward the right-angle bend in said conduit;
  a second cylindrical electrode wrapped around another leg leading away from the right-angle bend in said conduit;
  means for applying rf-energy to said first and second electrodes in series relationship in a manner to generate a visible emission spectrum favoring nitrogen from the excited gaseous mixture in said conduit;
  radiation detection means located along the longitudinal axis of the one leg close to said first cylindrical ground electrode and externally of said conduit for converting the light energy in the visible emission spectrum into electric signals;
  collimating means for said visible emission spectrum located along the longitudinal axis of the one leg and externally of said conduit between said conduit and said radiation detector;
  filter means for separating said visible emission spectrum into regions specific to predetermined spectral features characteristic of component gases therein located along the longitudinal axis of the one leg and eternally of said conduit between said conduit and said collimating means; and
  means for processing the electric signals from said radiation detection means into quantitative measures of at least the amount of nitrogen in said multigas mixture.

17. The apparatus of claim 16 in which said filter means separates the visible emission spectrum into three regions centered at about 360 nm, 620 nm, and 700 nm.

18. The apparatus of claim 17 wherein the multigas mixture comprises about ten to fifteen percent argon and the balance oxygen with traces of nitrogen.

19. A method for analyzing at least the amount of nitrogen in a multigas mixture that essentially comprises four to twenty percent argon and the balance oxygen with traces of nitrogen from a combined emission spectrum comprising the steps of:
   a. streaming a gaseous mixture through a conduit having first and second electrodes spaced apart therealong;
   b. applying rf-energy to such first and second electrodes in series relationship to generate a visible emission spectrum;
   c. collimating light energy emanating from such conduit along its longitudinal axis;
   d. filtering the collimated light energy to separate the visible emission spectrum into three regions centered at 358 nm, 617nm and 700nm;
   e. detecting light energy in each of said three separated regions of the visible emission spectrum and converting the same into electric signals; and
   f. processing such electric signals to derive a quantitative measure of the amount of nitrogen in the mixture.

20. The method of claim 19 where in the multigas mixture comprises about ten to fifteen per cent argon and the balance oxygen with traces of nitrogen.

* * * * *